(12) United States Patent
Beck

(10) Patent No.: US 8,674,330 B2
(45) Date of Patent: Mar. 18, 2014

(54) PRACTICAL DESIGN FOR A WALK-AROUND, HANDS-FREE RADIATION PROTECTIVE SHIELDING GARMENT SUSPENSION APPARATUS

(71) Applicant: Thomas J. Beck, Cantonsville, MD (US)

(72) Inventor: Thomas J. Beck, Cantonsville, MD (US)

(73) Assignee: Bar-Ray Products, Inc., Littlestown, PA (US)

( * ) Notice: Subject to any disclaimer, the term of this patent is extended or adjusted under 35 U.S.C. 154(b) by 0 days.

(21) Appl. No.: 13/833,476

(22) Filed: Mar. 15, 2013

(65) Prior Publication Data

US 2013/0270462 A1    Oct. 17, 2013

Related U.S. Application Data

(63) Continuation-in-part of application No. PCT/US2012/026054, filed on Feb. 22, 2012.

(60) Provisional application No. 61/445,250, filed on Feb. 22, 2011.

(51) Int. Cl.
  *G21F 3/02*      (2006.01)
  *G21F 3/025*     (2006.01)
  *F16M 11/42*     (2006.01)

(52) U.S. Cl.
  USPC ............... 250/516.1; 250/519.1; 211/85.29

(58) Field of Classification Search
  USPC .................... 250/516.1, 519.1; 211/85.29
  See application file for complete search history.

(56) References Cited

U.S. PATENT DOCUMENTS

| | | | | |
|---|---|---|---|---|
| 7,973,299 B2 * | 7/2011 | Rees | ............ | 250/516.1 |
| 8,558,204 B2 * | 10/2013 | Rees | ............ | 250/516.1 |
| 2011/0163248 A1 * | 7/2011 | Beck | ............ | 250/516.1 |

* cited by examiner

*Primary Examiner* — Nikita Wells
(74) *Attorney, Agent, or Firm* — Barry G. Magidoff; Paul J. Sutton

(57) ABSTRACT

A rollable structure for suspending a heavy radiation protective garment so as to allow easy movement in a clinical environment subject to exposure to x-radiation. The structure comprises a vertically extending frame that is attachable to a user, and that permits the user to move freely around the clinical environment and to perform clinical duties without having to bear the weight of the shielding garment. The frame is vertically adjustable, and supports upper shield support surfaces for supporting the shoulder portions of a radiation protection apron. The upper support surfaces extend outwardly from the vertical frame. A rollable lower support frame for the vertical support frame is provided that includes a first lower frame extending forwardly from the vertically extending frame. A second lower frame for supporting the vertically extending frame is located at a position other than forwardly of the vertically extending frame. A pair of casters is provided at the lower end of each of the lower frames. A midbody attachment is provided for securing a flexible belt between the vertically extending framework and the use to allow the user to walk with the framework without the use of his hands.

20 Claims, 17 Drawing Sheets

PRACTICAL DESIGN FOR A WALK-AROUND, HANDS-FREE RADIATION PROTECTIVE SHIELDING GARMENT SUSPENSION APPARATUS

This application is a continuation in part application of copending PCT/US2012/026054, filed on Feb. 22, 2012 and of U.S. Provisional Patent Application No. 61/445,250, filed on Feb. 22, 2011. This application is being filed under 35 U.S.C. §111(a).

The present invention relates to a practical design for suspension apparatus to relieve the weight of heavy shielding garments on staff working in a clinical environment subject to exposure to x-radiation during medical procedures involving significant x-ray exposure to the worker. The device suspends the weight of the radiation shield on a mobile carriage that permits him or her to walk freely around the working environment. It is easily adjusted to the size of the wearer, incorporates a transparent face shield and permits unimpeded normal clinical operations in a surgical sterile field with disposable sterile drapes or other shield. Several preferred embodiments are described, a light-weight version that can suspend the weight of conventional one-piece protective garments for use by attendant staff, and a second more robust version for the physician performing the procedure that permits easy entry and exit from a sterile draped special purpose shield.

BACKGROUND OF THE INVENTION

In the medical field, personnel are often required to work in close proximity to patients undergoing imaging and therapeutic, or surgical, procedures involving x-rays. The hazard to the worker arises (mainly) from x-rays scattered by the patient's body toward the worker. To minimize exposure the worker traditionally wears a radiation shielding garment that places a protective barrier between the scattering tissues of the patient and the body of the worker. Traditionally such garments are made from a flexible rubber or polymer material within which is embedded fine, particulate lead, or other heavy elements that are good absorbers of x-rays. Unfortunately such garments, containing sufficient heavy metal to be safe, are heavy, and can cause significant orthopedic injury to the wearer with daily use over a working lifetime. In fact, such orthopedic injury from repeated use of heavy protective garments significantly limits the working lifetime in medical professions using x-rays. Several suspension designs have been previously developed but generally use either a ceiling suspension or a floor mounted frame, requiring a specially designed protective curtain. Devices that suspend the weight of the protective curtain from the workers body can greatly reduce the risk of orthopedic injury and have been developed by a number of investigators. For example, see U.S. Pat. No. 4,254,341, Herr et al., 1981: Radiation Protection Device Particularly for Medical X-Ray, Radiation Therapy and Diagnostic Use; U.S. Pat. No. 4,581,538, Lenhart, 1986: Radiation Shield; U.S. Application 2009/0256044 A1: Suspension System and Method; U.S. Pat. No. 5,015,864: Maleki 1991: Mobile Radiation Shield; and U.S. Pat. No. 5,185,778, Magram, 1991 X-ray Shielding Apparatus.

Objects of this Invention

An ideal device should provide equal or better protection than unsupported shielding, since its weight need not be limited by what even the weakest or smallest wearer can bear. It should be relatively unobtrusive and easily mobile in all horizontal directions, on that normal operations are easily accomplished without obstructing other functions in the clinical environment. The present device is a practical, easily manufactured version that can suspend the presently, readily commercially available shielding garment on a strong, easily mobile, floor-mounted frame. One preferred embodiment can suspend the weight of conventional shielding apron with a light-weight aluminum frame, while a second preferred, more robust embodiment can support a larger heavier garment that protects more of the body or protects to a greater degree than is convenient with unsupported shielding garments. The frame preferably contacts the waist of the wearer, most preferably at the front and at the back, ensuring that it moves freely with the operator, without restricting movement in any direction. It further allows the wearer to work immediately adjacent the patient without fear that the frame will become unbalanced and fall on the patient.

It is therefore an object of this invention to suspend the weight of heavy protective radiation garments worn in clinical environments so that the weight is not borne by the body of the wearer. It is a further object of this invention to simultaneously provide an equal or greater degree of radiation protection than is practical to provide in an unsuspended radiation garment, without limiting mobility of the clinician. It is a further object of the invention to provide a suspension apparatus that does not require an overhead crane and that does not restrict the free movement of the wearer in any horizontal direction. A yet further object is to have a stable support that allows working immediately adjacent a patient.

Such a design in order to be useful must meet the following requirements. First, it needs to have a means to achieve a quick, easy hook-up and release of the supported garment. It cannot interfere with the surgical draping that ensures sterility of the operating field. It must be unobtrusive, and it must permit normal functions by the professional clinician at the tableside of a patient. It must be ultra-stable and fully mobile. It should move easily in all directions, without requiring significant additional effort by the wearer. It should preferably permit support of an optional face shield, and be usable by persons of a wide range of sizes, at least from 5 ft. to 6 ft., 6 ins, in height. The device should be able to accommodate users varying widely in girth by an adjustment mechanism or by providing shielding garments of different sizes.

GENERAL DESCRIPTION OF THE INVENTION

The above objects are all met by the present invention which comprises a highly mobile, structurally strong frame that supports a range of available radiation-absorbing shields but allows substantially complete freedom of movement by the user around a clinical environment subject to exposure to x-radiation requiring even the heaviest, most effective shields. The frame virtually eliminates the weight of the heaviest lead, or other heavy metal containing apron from weighing on the user. It does so without restricting movement, and preferably has sufficiently large rolling supports so as not to be obstructed by floor irregularities, when moved. It preferably can adjust vertically for a wide range of user heights, e.g., of at least from 5 ft. to 6 ft., 6 ins. (152-198 cm). Totally hands-free operation is accomplished with contacts, e.g., a belt that attaches to the frame, preferably at the waist and at the small of the user's back. It preferably also includes an optional face shield to protect the head and neck of the user.

The full weight of the radiation shield and frame is rollably supported, e.g., on four support casters on a base-frame that surrounds the user. The frame is well balanced and remains stable during all normal operations. Preferably, this is achieved by providing a frame that allows the front rolling support, e.g., a wheel, or casters, to extend forward of the anticipated center of gravity as the user may lean forward over a patient. The structure of the light-weight embodiment can be fabricated from aluminum alloys. Where an especially heavy shield is required, the light-weight support can be used with counterweights supported on the rearmost portion of the frame.

The preferred embodiment for the physician performing a surgical procedure using, e.g., fluoroscopy is preferably more robust, with a structure that can be fabricated of stainless steel or a combination of powder coated steel and stainless steel. It is understood that as stronger and lighter materials become available, any such desirable materials can be used for fabricating, all or part of the frame.

Preferably, the frame of the light weight embodiment can be easily folded flat when not in use or for shipment; the stronger and usually heavier embodiment of the frame, can be disassembled for shipment into two or more main parts that are easily re-assembled by the user without requiring specialized tools. The rear, primary support structure of all embodiments of the frame is vertically adjustable relative to the wheel base, to enable the frame to be used by a wide range of personnel, of varying heights, e.g., of from less than five (5) feet to at least about six (6) feet six inches. The vertical adjustments can be carried out purely manually or with the aid of, for example, a pneumatic, hydraulic or rack and pinion gear system or a counterweight with or without assisting constant-force springs. A preferred system for the heavier embodiment of this structure comprises a counterweight system to allow for easier lifting of the heavy materials. Another useful system that may be incorporated into the light-weight embodiment incorporates a simple pneumatic system as described below. Both mechanisms are well known and are generally readily available for the purpose.

The frame further provides for a radiation-absorbing, transparent face shield, to protect the neck and head areas from the radiation, and which is totally supported by the support frame. The face shield in some preferred embodiments may be preferably rotatable, so that it may be flipped upward to permit easier entry and exit from the frame.

The user of the light-weight embodiment would initially adjust the height of the upper supports so that they are above his or her shoulders, and the height of the waist-belt connector to the level of their waist. The user would don a conventional lead apron and attach the weight supporting hooks on the support frame to shoulder supports, then would attach the belt on the waist support around their waist.

In on of the more robust embodiments, the mobile shield would first be draped with a sac-like sterile drape that envelops the specialized shield with arm holes for the user and a sterile wrapping around the waist strap. The sterile draped shield can then be swung outward on the pivoting support so that the shield can be entered from its rearward aspect by the user wearing the sterile gown and gloves. The wearer then attaches the sterile draped belt around their waist and swings the shield back into position for use. Alternatively, the frame can be provided with contact surfaces that would be less restrictive than a belt, but would allow the user to move the frame in substantially any horizontal direction around the patient.

Exemplary embodiments of the present invention are depicted in the following drawings:

GENERAL DESCRIPTION OF THE DRAWINGS

Figure 17:
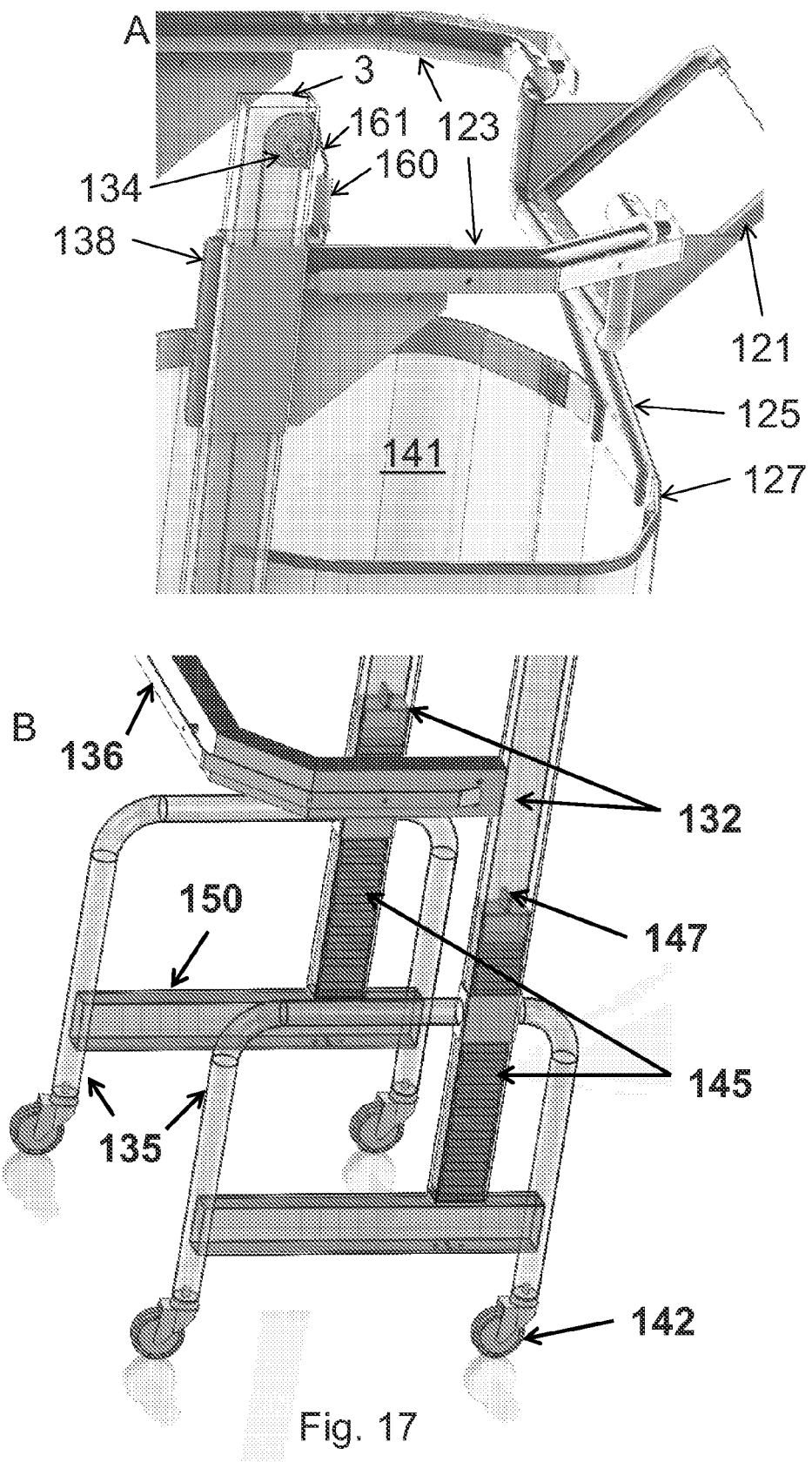
Figure 18:
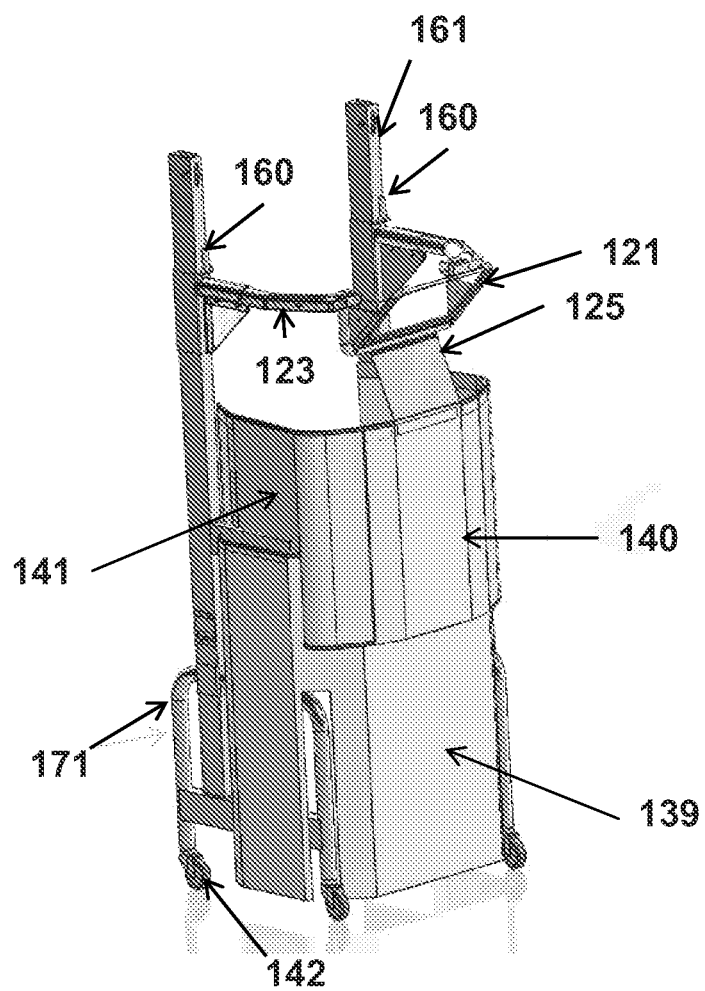

FIGS. 16A,B depict a more robust frame, without a supported curtain shield, from a front perspective and perspective view, respectively;

FIGS. 17A,B depict a more robust frame, without a supported shield, from a front perspective and perspective view, respectively; and FIG. 18 depicts the more robust frame of this invention supporting heavy panels of the radiation protective material.

DETAILED DESCRIPTION OF THE DRAWINGS

The drawings depict two preferred embodiments of the adjustable, movable support frame of the present invention. FIGS. 1-8 depict the adjustable, movable support frame of the light-weight embodiment of the present invention, which is generally indicated by the numeral 1. This light weight frame can be preferably fabricated mainly of light-weight aluminum tubing, which includes a vertical height adjustment by virtue of the telescoping tubing 2. Attached to the tubing is an independently height adjustable rigid tether 5, attaching to the back of the wearer's waist by a waist strap. The apron 8 is supported from a pair of flexible suspension beams 10, maintained under tension by the weight of the apron and held on the upper, forward ends of the telescoping tubes.

The entire frame is supported on casters, a rear pair 12 substantially directly under the main vertical support tubes 2, and a second pair of casters 14 at the bottom of forwardly projecting curved rods 11 rigidly attached, or optimally adjustable as to height, secured to the vertical tubes 2. In this manner, putting forward torque on to the support frame, when the worker leans forward, will not tip over the frame. As a further means to balance an especially heavy shield apron, counterweights 51 can be added and supported on the rear frame, as shown. By stacking individual weights of desired increments, a range of weights can be counter-balanced by adding or subtracting the individual weights.

Figure 1:
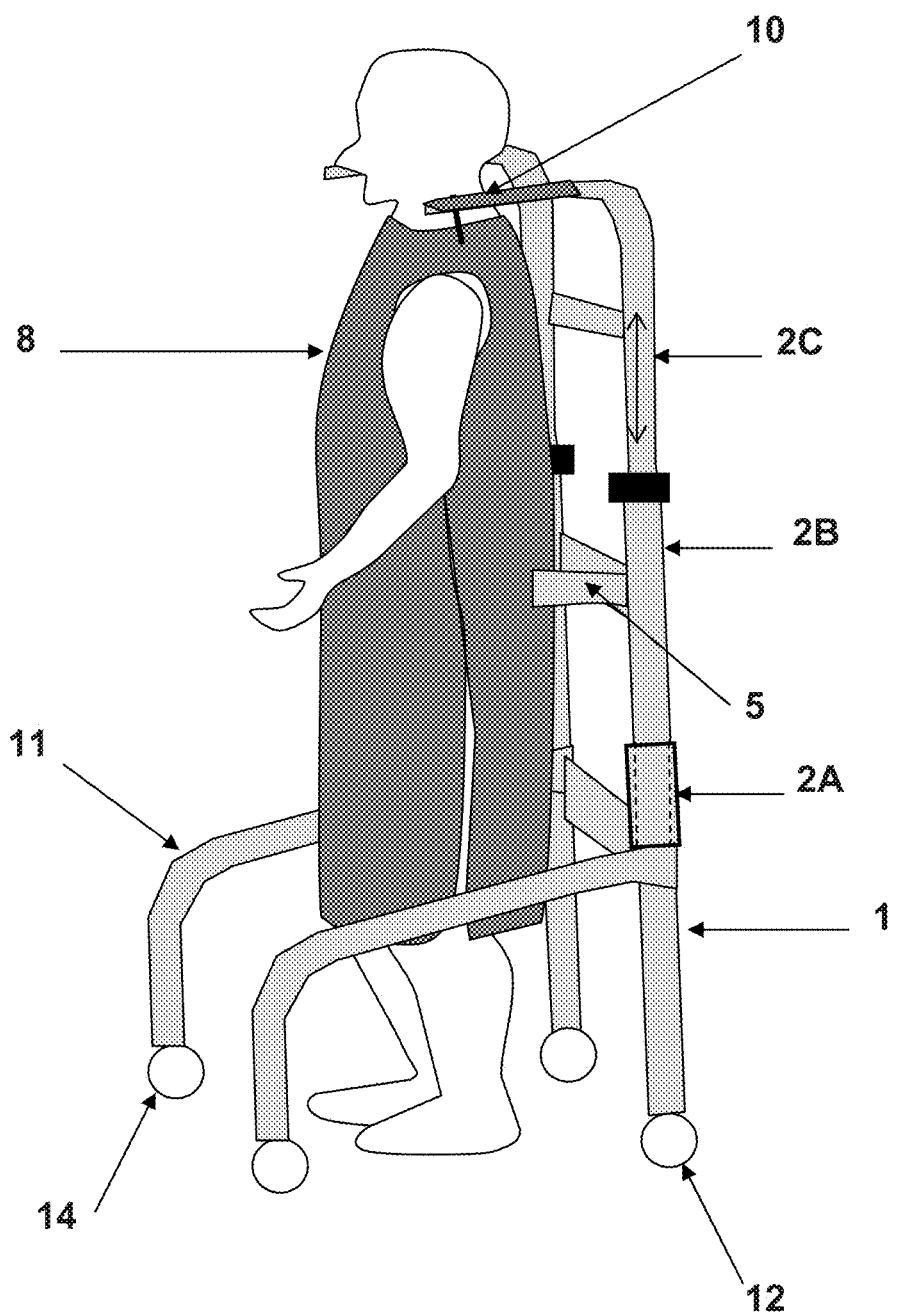
FIG. 1 is an isometric drawing diagrammatically showing the support device of the light-weight embodiment supporting a radiation protection apron and a user in place.
Figure 2:
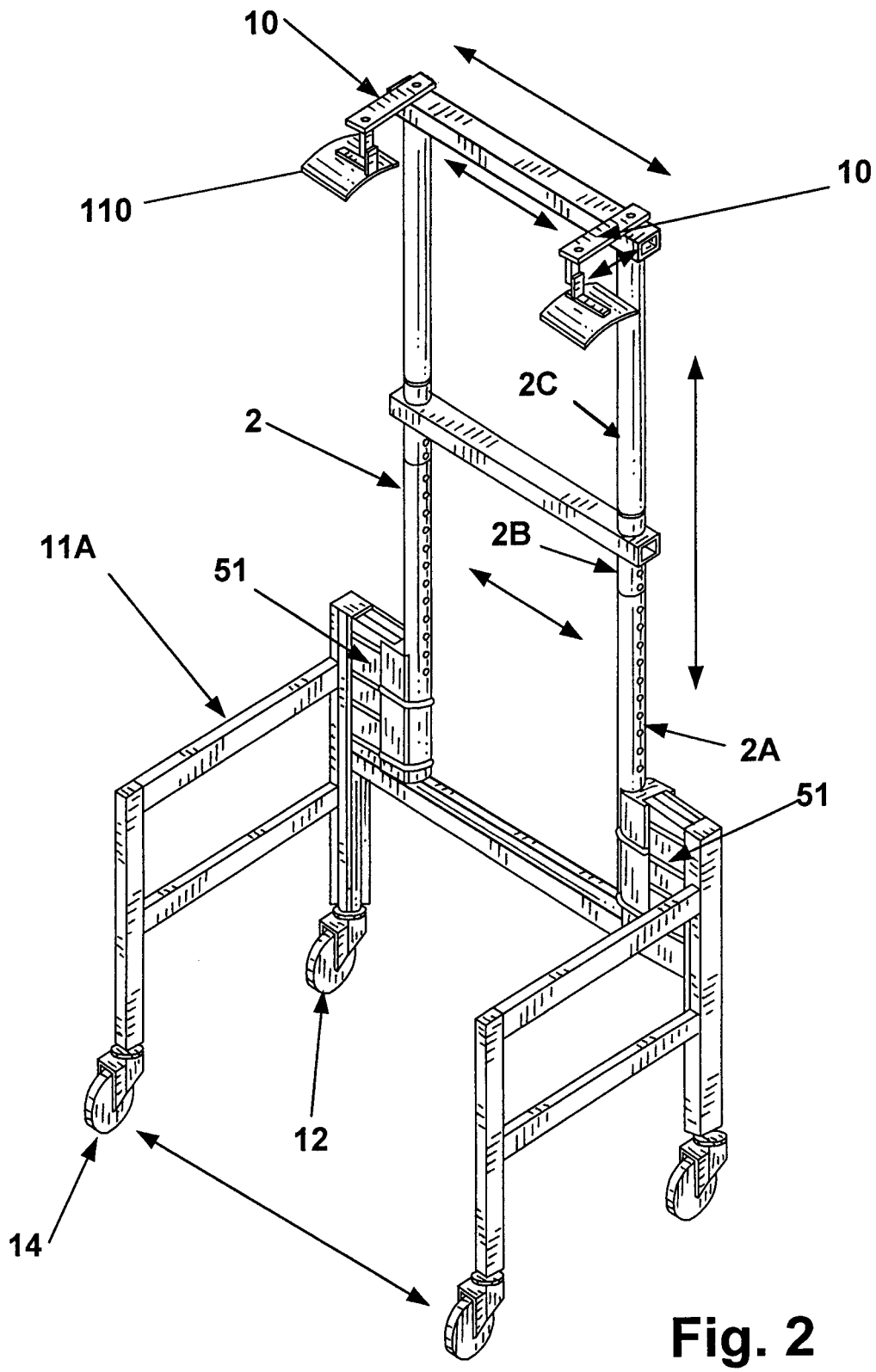
FIG. 2 is an isometric drawing of a second light-weight embodiment of the bare support frame showing size adjustments that are possible, and including an adjustable counterweight system.
Figure 3:
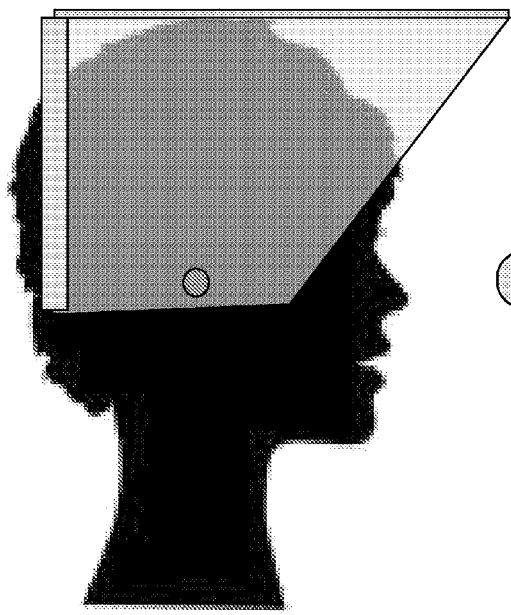
FIGS. 3, 4A and 4B are side and top views showing one embodiment of a face shield for use on the support frame of a light-weight embodiment of the present invention
Figure 4A:
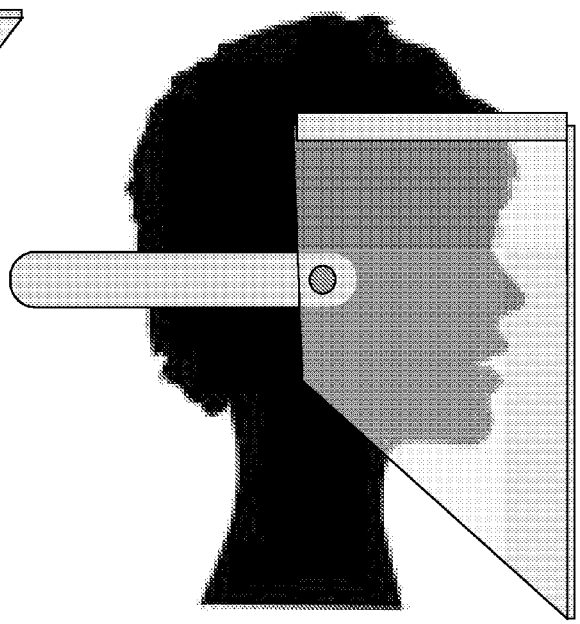
Figure 4B:
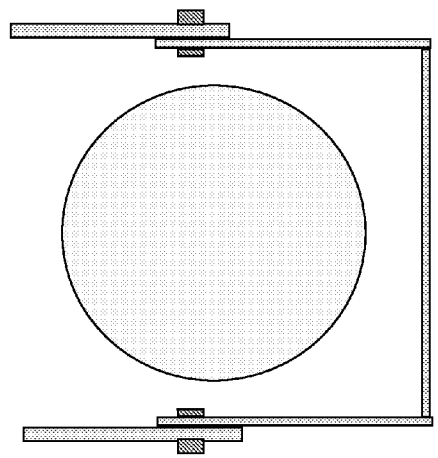
Figure 5:
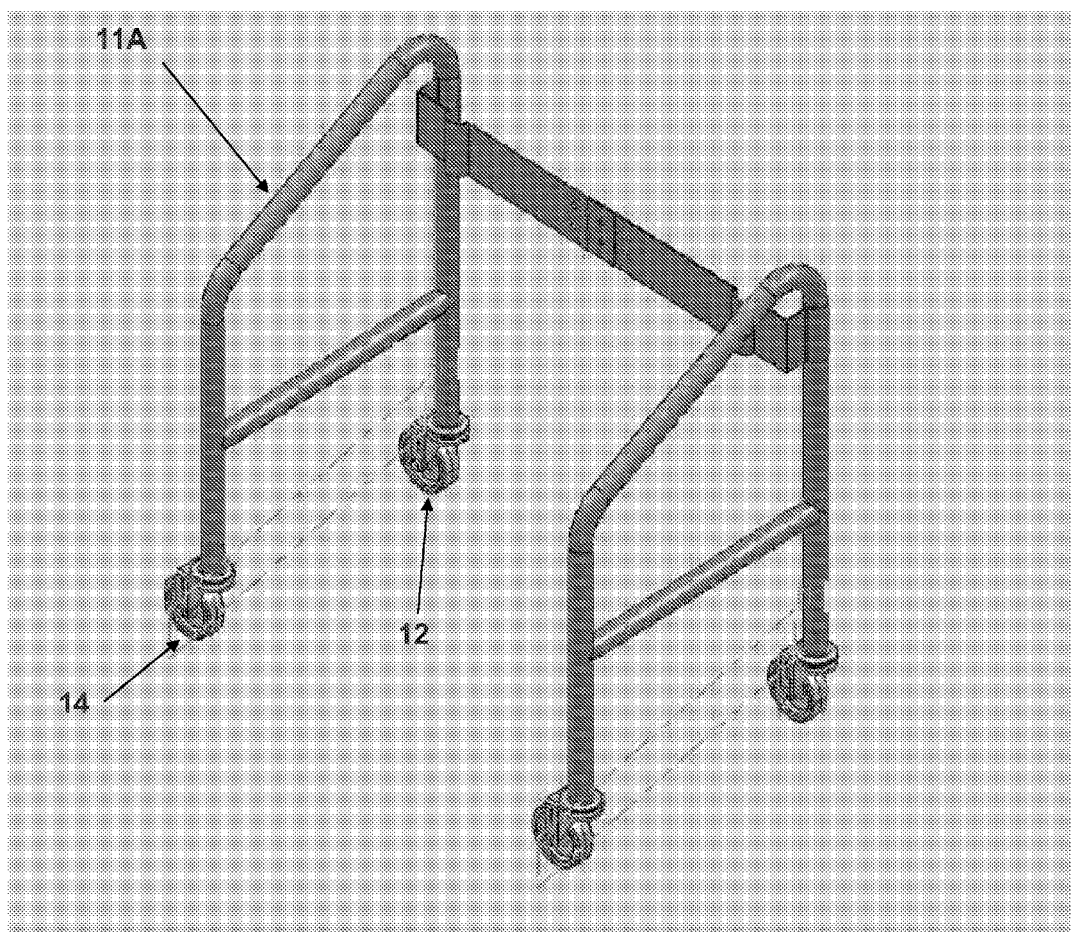
FIG. 5 is an isometric drawing of merely the support caster frame of a light-weight embodiment of the bare support frame.

Preferably, vertical adjustment is provided by the telescoping tubes 2A, 2B and 2C, for individual heights from at least 5 ft, to 6 ft., 6 ins. Other adjustments are indicated in FIG. 3 by arrows, including sideways adjustment to broaden the width of the frame, and depth adjustment to support the apron shield 8 at different distances from the primary rear frame support. The frame of the light weight embodiment can preferably be folded flat for shipment, the front wheel frames folding inwardly against the rear support frame, as shown in FIG. 5. Except for telescoping tubes and some minor parts, preferably all stainless steel construction is used for a second lightweight embodiment, of FIG. 7. The first embodiment is preferably constructed primarily of aluminum alloy. All components, in either embodiment, are designed so that it can be constructed from commercially available materials.

The pneumatic elevating mechanism of FIGS. 8A-G works with the telescoping tube set of the vertical supports of the primary support structure and includes: a solid seal bonded to the bottom of the bottom tube with an air hose fitting. A tube connected to the fitting can carry pressurized air from a hand air pump 79 or an electrically powered pump. The upper telescoping tube is sealed at the bottom using a solid seal bonded to the bottom of each upper tube, and includes an O-ring around the outer circumference of the seal. The edge seal with a center hole is bonded to the bottom of the middle tube and includes an o-ring around the outer circumference of the edge seal to seal the middle tube to the lower tube. The upper ends of the bottom and middle tubes have a central opening to allow the next higher tube to move in a longitudinal direction, but will act as a stop to prevent the next higher tube from coming out of the lower tube. The solid upper seal acts as a pressure surface to move the upper tube and then the lower tube as air pressure in the inner chambers is increased. It is noted that the telescoping tubes 2A-2C, can have a round, or circular cross-sections, or a rectangular, or square cross-sections, as long as the tubes can closely slide within each other.

Figures 6A, 6B:
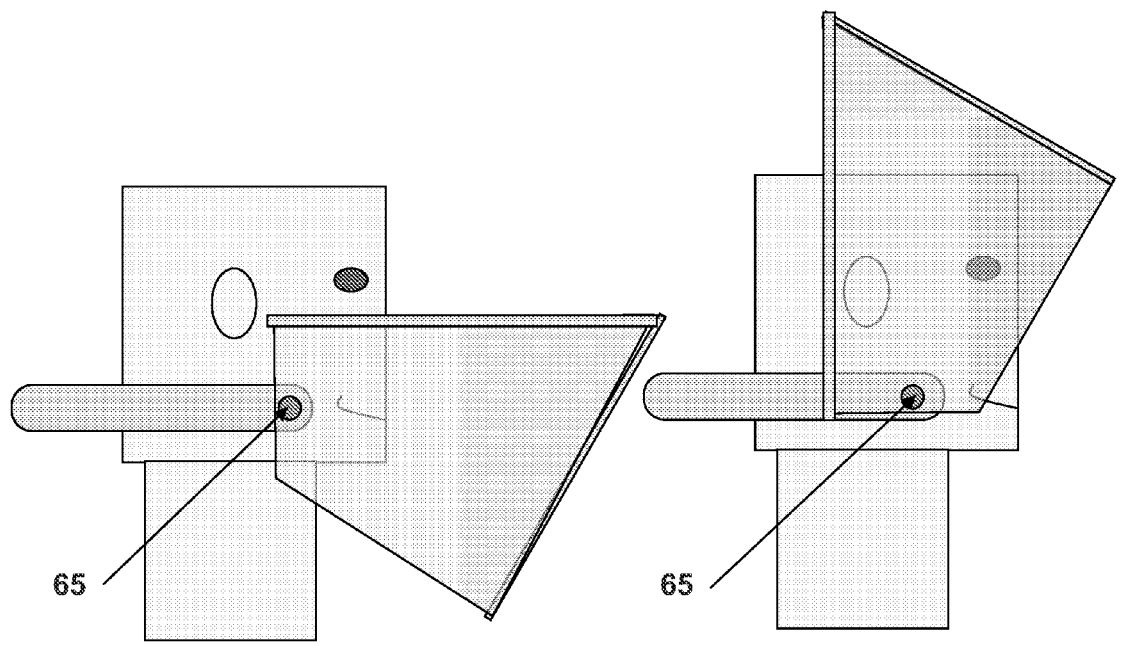
FIGS. 6A and 6B show another embodiment of a face shield.
Figures 7, 7A:
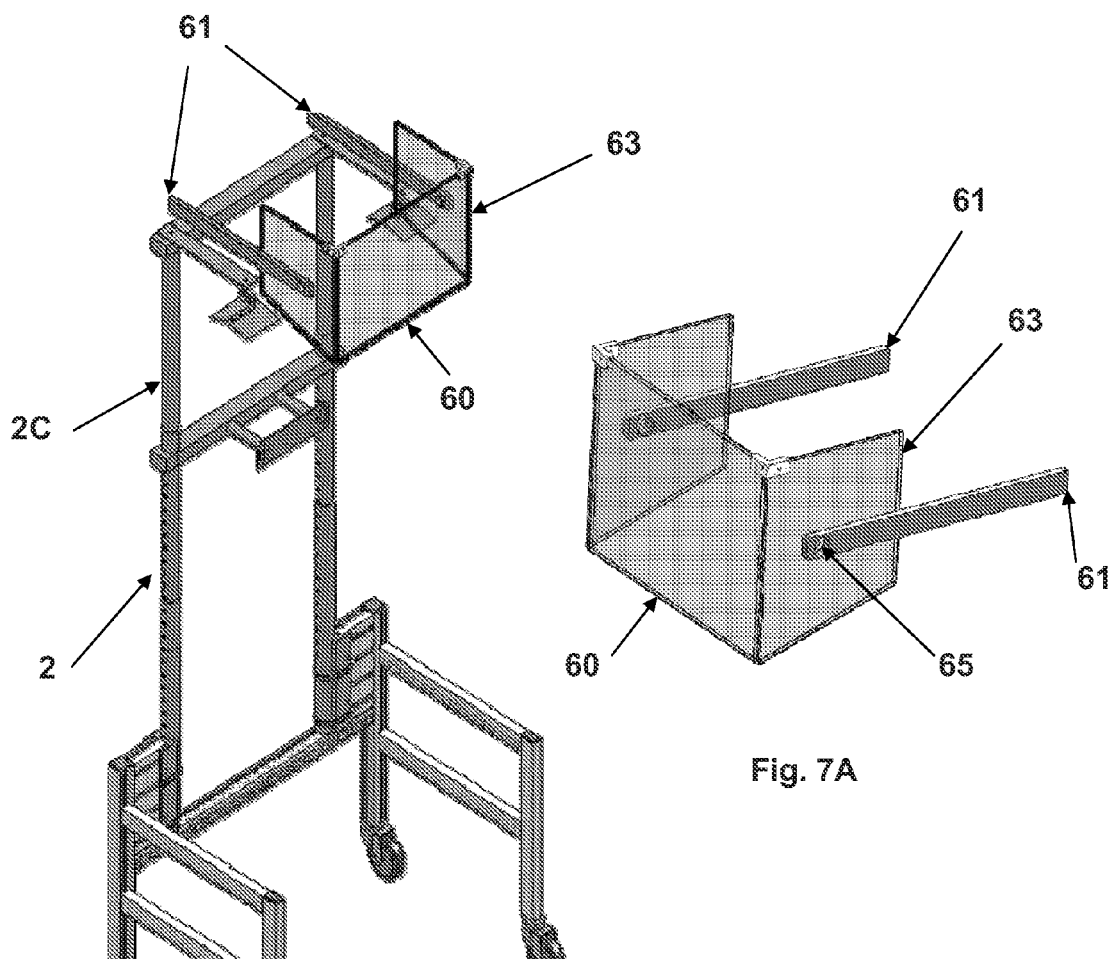
FIG. 7 is an isometric drawing of a bare support frame with an attached embodiment of the face shield.
FIG. 7A, is an isometric drawing of an enlarged view of the face shield of FIG. 7
Figure 8:
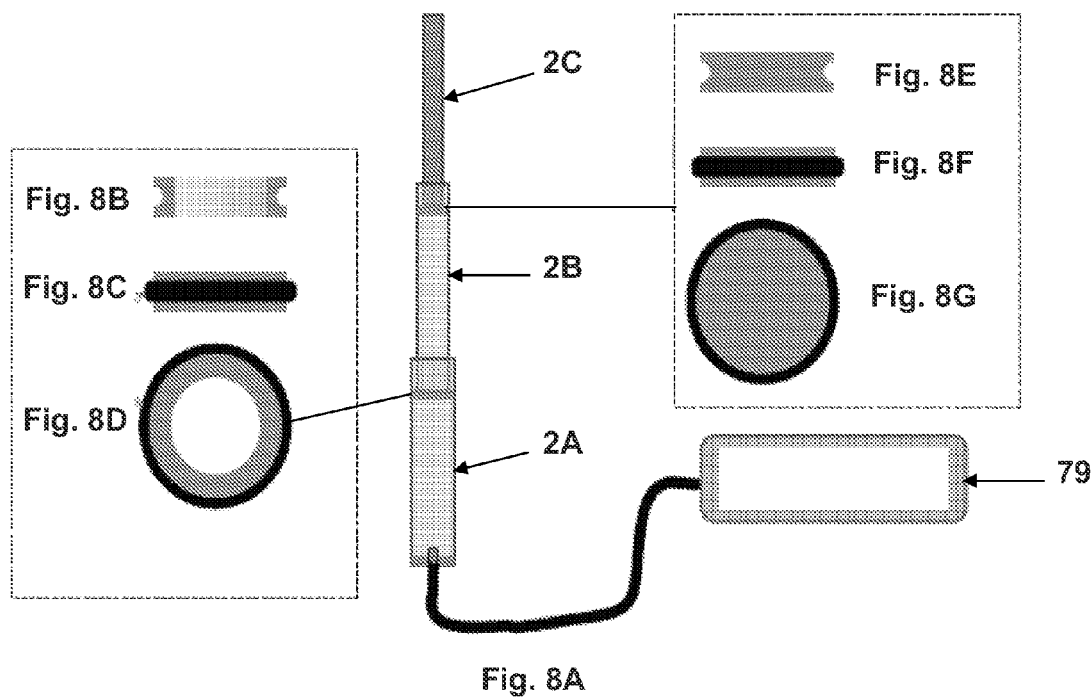
FIGS. 8A through 8G are diagrammatic drawings showing a pneumatic elevating mechanism for assisting in vertically adjusting the support frame for different height users.
Figure 9:
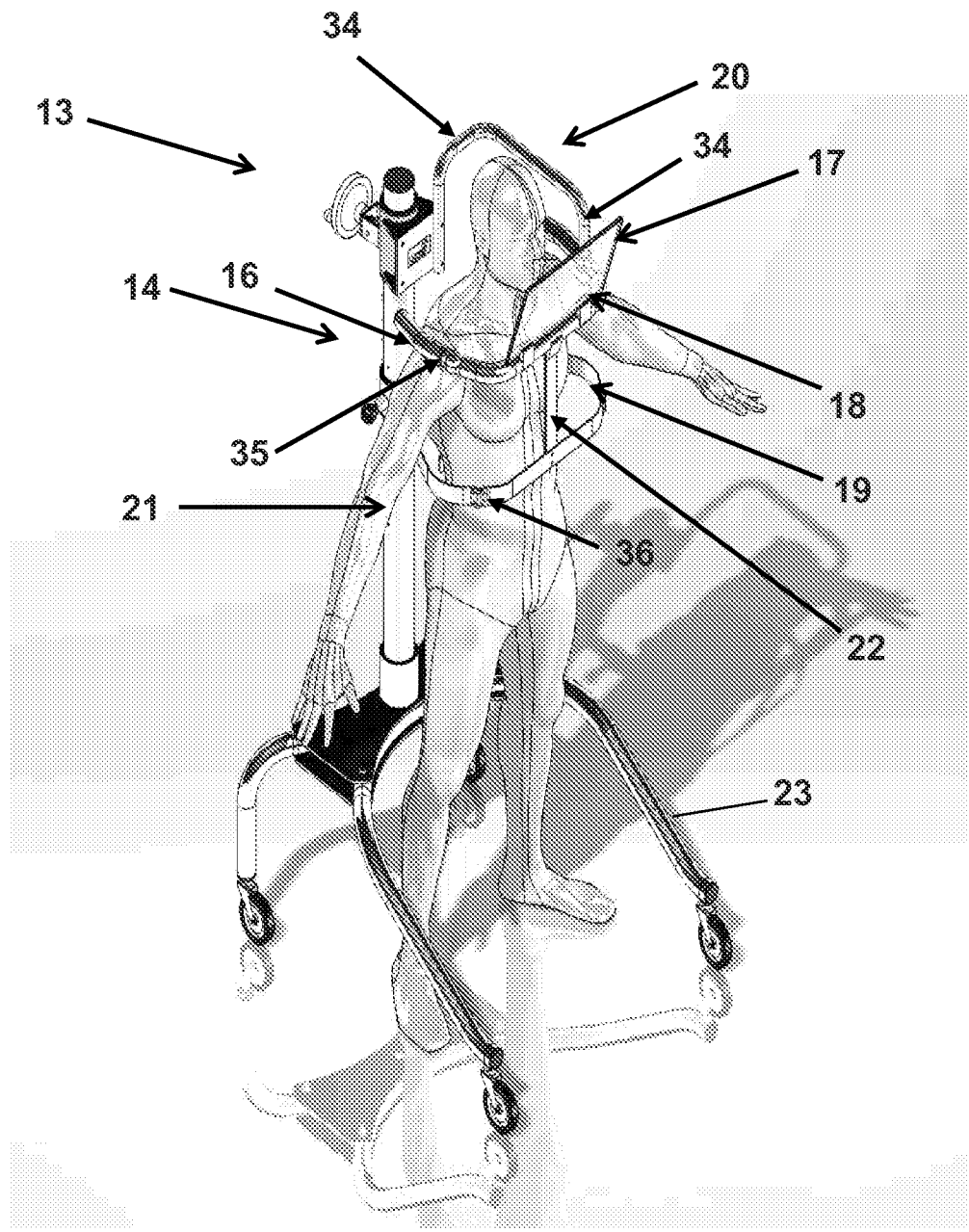
FIG. 9 is an isometric drawing of a more robust embodiment showing the support frame and a user in place with a face-shield but with the protective curtain removed.
Figure 10:
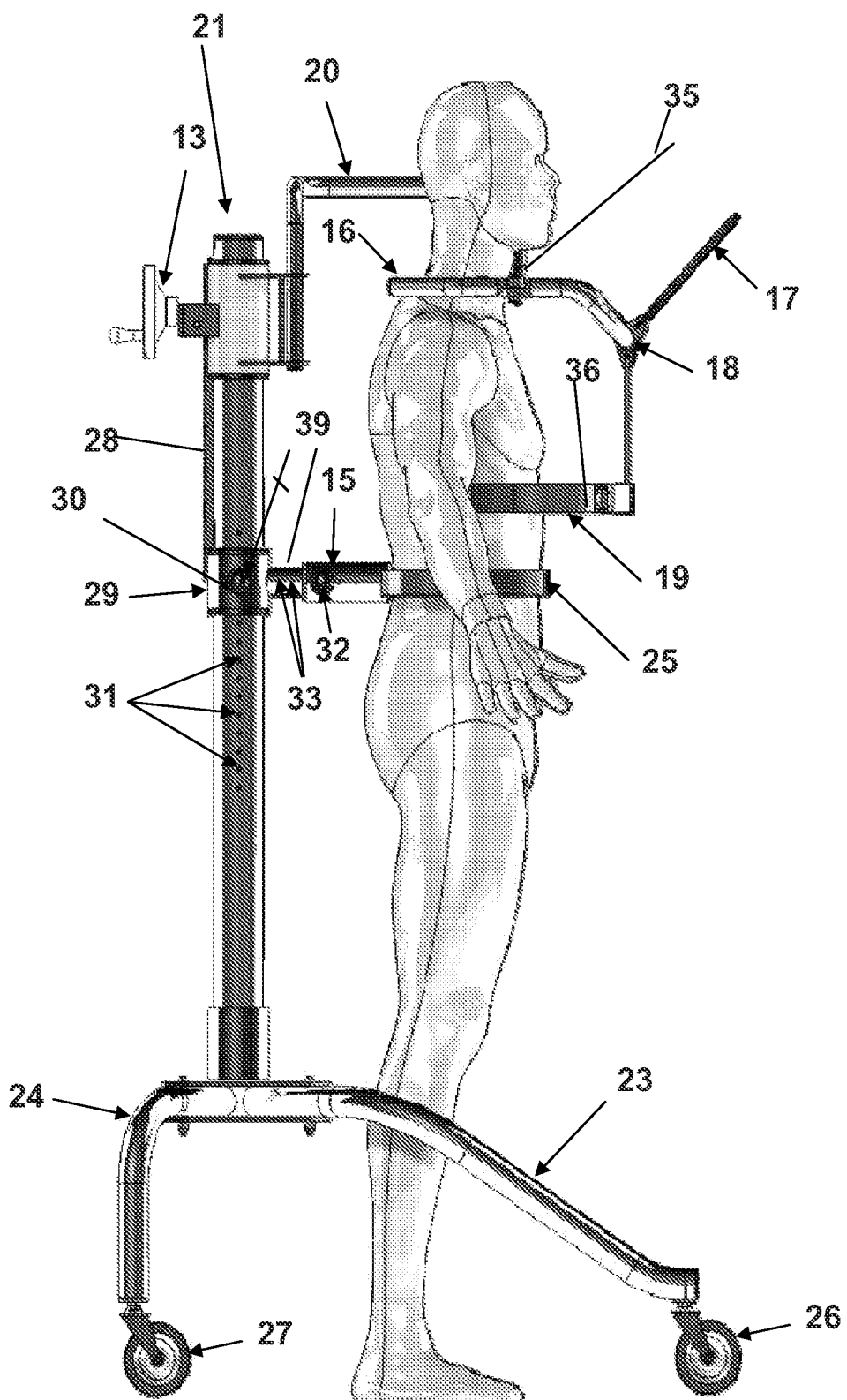
FIG. 10 is a side elevation view of the robust embodiment of FIG. 9.

Face shields, such as those shown in FIGS. 4A-C, 6A-B, and 7, are transparent to visual light and can be made of tempered or laminated lead glass or lead-filled acrylic sheet, so as to substantially reduce the passage of ionizing radiation such as x-rays. Various shapes are possible, and as shown several are available, their selection depending upon personal preference and the particular procedure for which they are used. A face shield, for example as generally indicated by 60, in FIGS. 7, 7A, is supported by arms 61 from the upper portion of the support frame 2, and should be rotatable relative to its support frame, up and down, e.g., as shown in FIGS. 6A-B, and 7, about a pivot member 65 to permit easy entry. The shield should allow for easy cleaning or removing any material adhered to the visually transparent shield. In the light weight embodiments, the shield can be connected to the main structure by its supports 61, connected to the vertical support structure at its upper end and movable with the vertical support structure.

Cable suspension for the supported apron in the lightweight version is supported at its shoulders by the curved surfaces suspended forwardly of the main support structure, but rearwardly of the forwardly projecting front wheels; preferably rearwardly of the center of gravity of the casters support frame. This avoids any forward torque that might otherwise cause the structure to topple forwardly over a patient. The frame connecting the forward pair of wheels to the main support frame is preferably sufficiently low as to be able to fit under an operating or radiology table. The shoulder portions of the apron fit over the curved surfaces 110 supported from the top of the vertical frame. The support surfaces are flexibly supported from the upper end of the main support frame. These support surfaces can be made to be independently vertically adjustable with respect to the support frame.

Preferred embodiments for use by, e.g., a surgeon for lengthy exploratory surgery using fluoroscopy, are shown in FIGS. 9-15. These embodiments are heavier and more robust to provide stability for a swing-out shield that permits him or her to enter the sterilely draped shield, from its rear aspect, without contaminating the sterile gown and gloves. An upper shield support frame 16 is supported by an arm 20 extending as a cantilever from, and movably supported by, the main vertical support 21, via a geared elevation mechanism, generally indicated as 13; this geared mechanism is mounted on the main cylindrical support column 21, that attaches to the caster-supported base, generally indicated as 23.

Adjustment for the height of the user is provided by the ratcheting rack and pinion gear mechanism, generally indicated as 13, that vertically adjusts the height of the cantilevered support arm (20) from which the upper (16) and lower (19) shield supports are mounted. The lower shield support (19) is rigidly connected to, and supported by, a vertical strap 22, extending from the upper support (16) which attaches to the support arm with a pivoting mount 34, that permits the upper and lower supports with the apron to pivot outward for ease of entry into the device. Further pivot points 35, 36 are optionally located at the outer portions of each of the upper 16 and lower 19 shield supports, to enclose the shield around the user after entry, and to swing outwardly to allow easy exit.

Further adjustment for height is provided by a sliding bracket 15 to which the waist belt 25 is attached. The bracket 15 is adjusted to the waist height of the user by the waist belt elevating mechanism 29 and locked into position by the locking member 30, which is spring loaded and fits into holes 31 formed into the vertical support 21. The bracket 15 incorporates a locking, horizontally telescoping element to adjust the distance of the user from the support column (21). The horizontal locking element 32 is spring loaded and fits into holes 33 formed into the horizontal tube 39 extending from the waist belt elevating mechanism 29. This allows the locking of the back of the belt a fixed distance from the vertical support 21.

A face shield 17 is rotatably supported on the upper shield support 16, from swivel joint 18. The shield 17 can swivel towards and away from the user.

Figure 11:
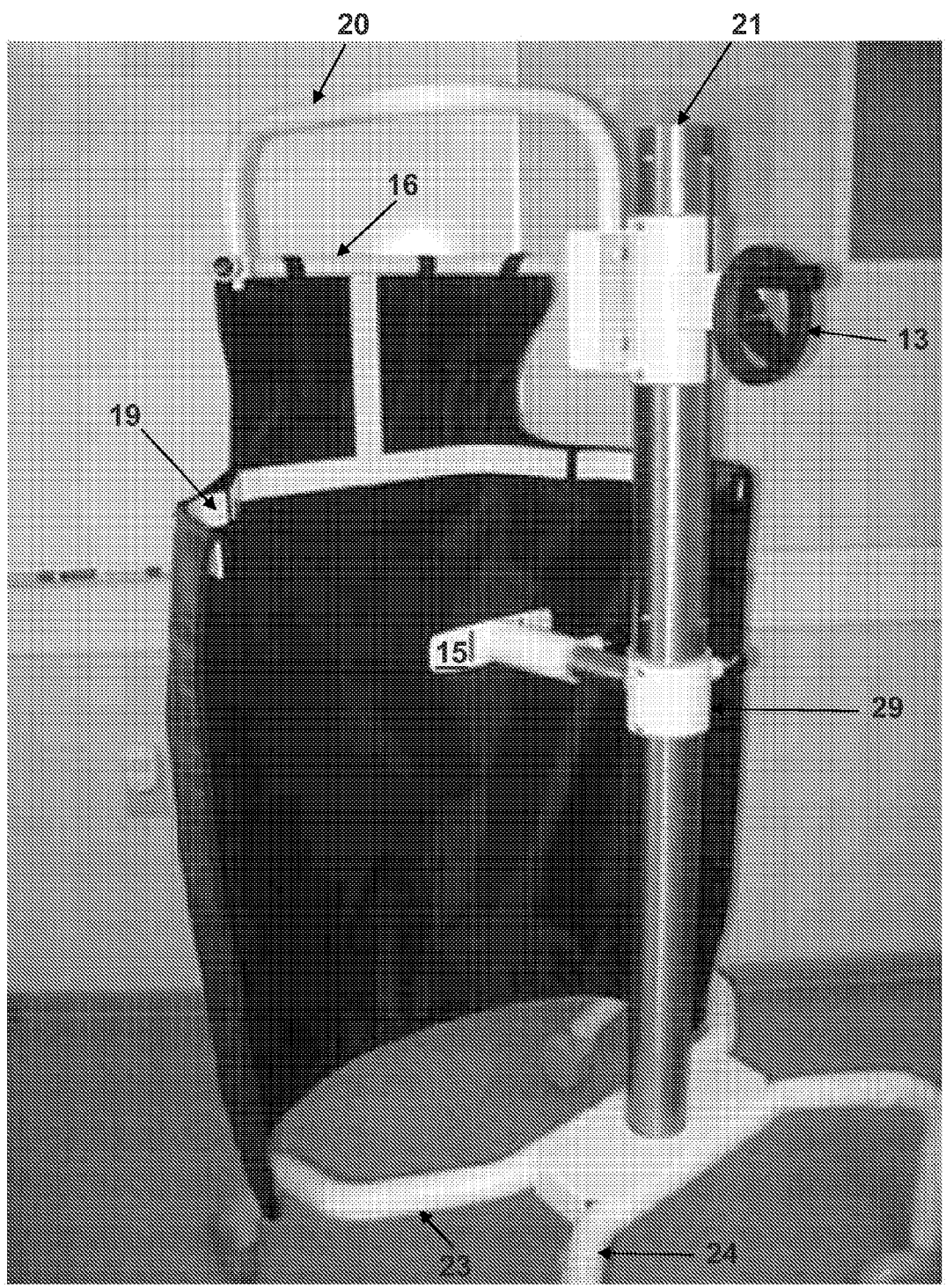
FIG. 11 is a view of the robust embodiment of FIG. 9, including a supported radiation shielding apron, as viewed from its interior.
Figure 12:
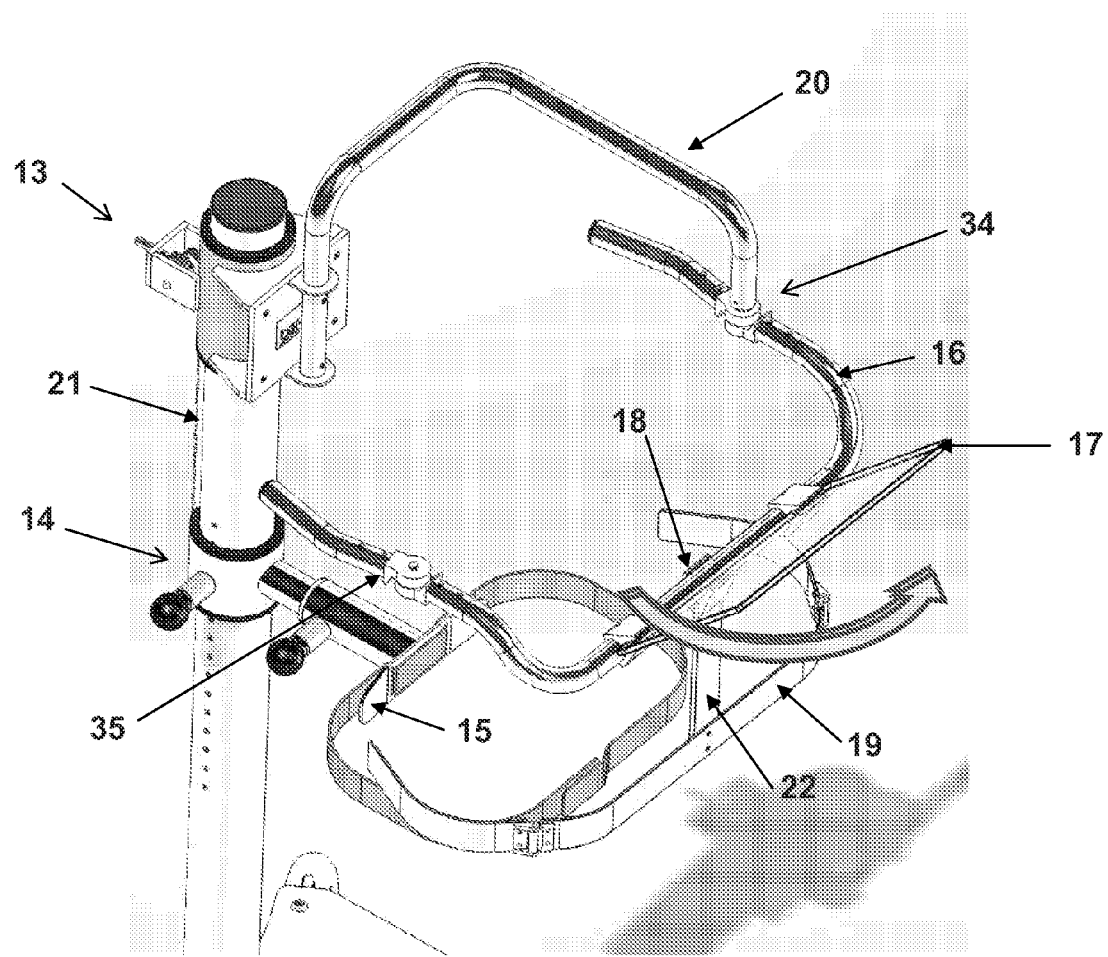
FIG. 12 is an enlarged isometric drawing, looking downwardly, of the upper and middle portions of the robust embodiment of FIG. 9, showing the elevating mechanism and the upper support frame.
Figure 13:
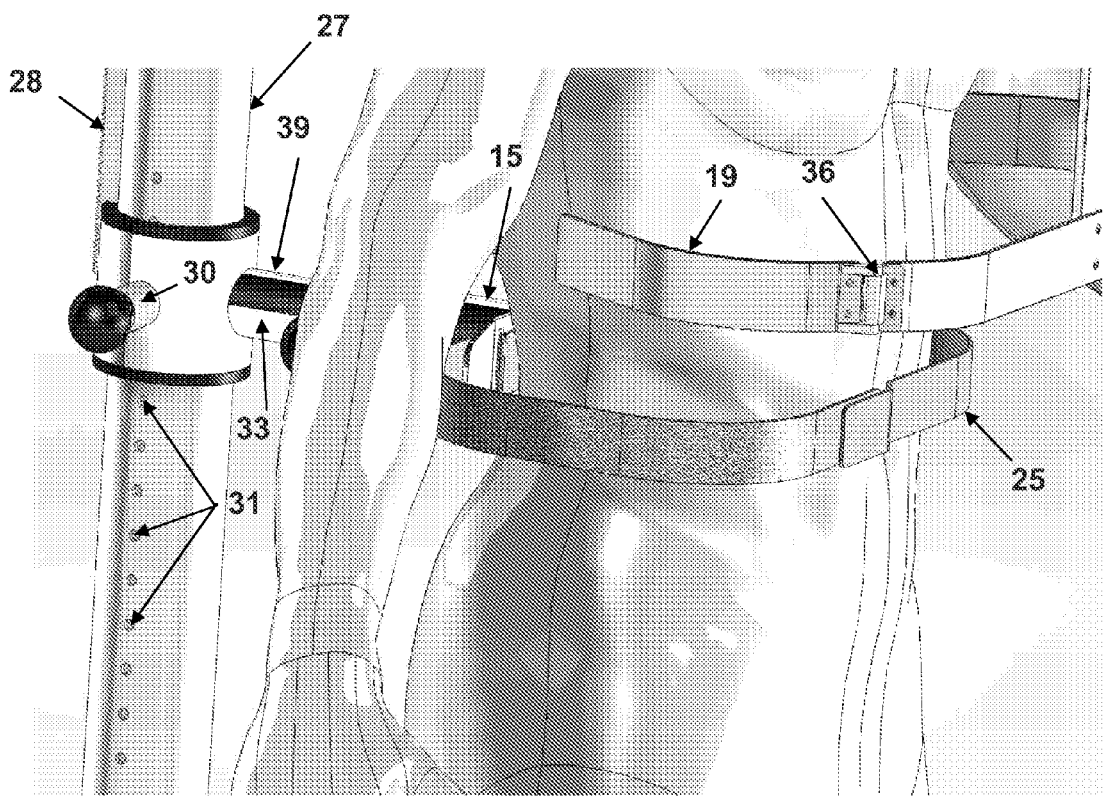
FIG. 13 is an enlarged isometric drawing with the operator of the central portions of a robust embodiment of the frame, from the front.

As is shown in FIG. 11, An apron shield can be supported from its upper edge by the upper shield support 16, and from the bottom of its arm cut-outs from the lower shield support. In this manner, the apron shield can be maintained away from the body of the clinician. The clinician can push the support around from the clinician's waist belt in substantially any horizontal direction.

Figure 14:
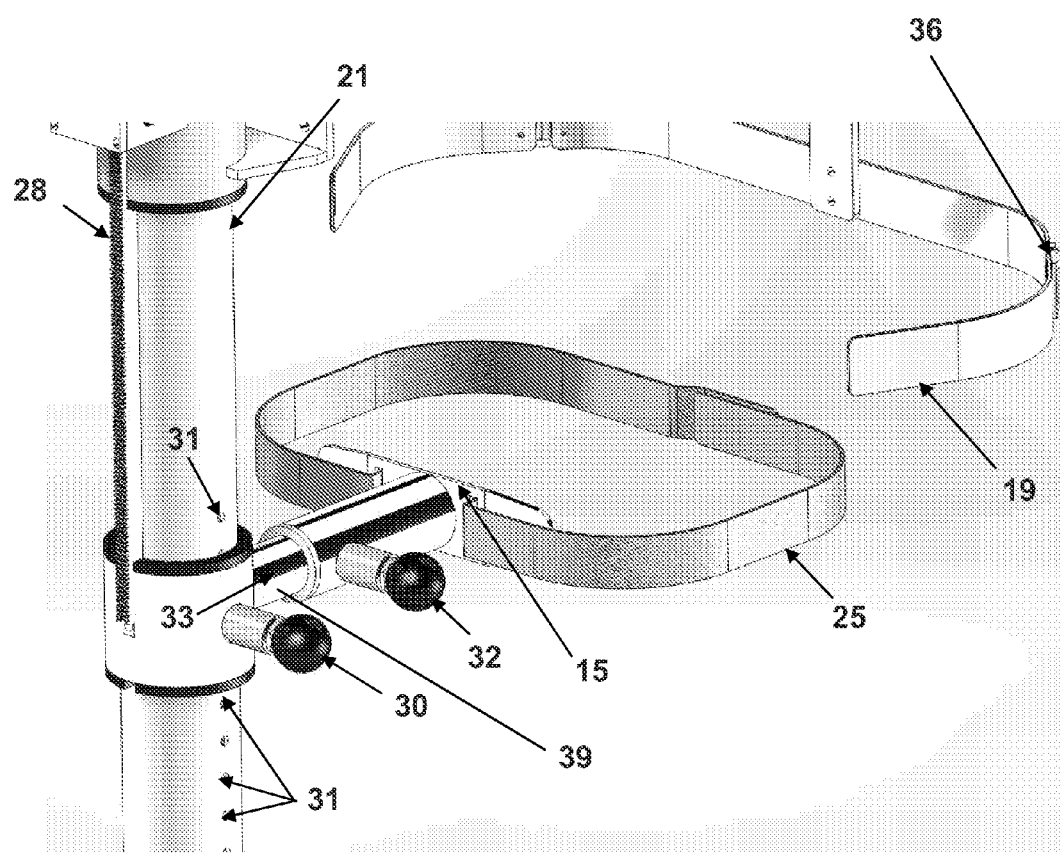
FIG. 14 is an enlarged isometric drawing of the central portion of a bottom detail view of the robust embodiment of FIG. 9, from the rear.
Figure 15:
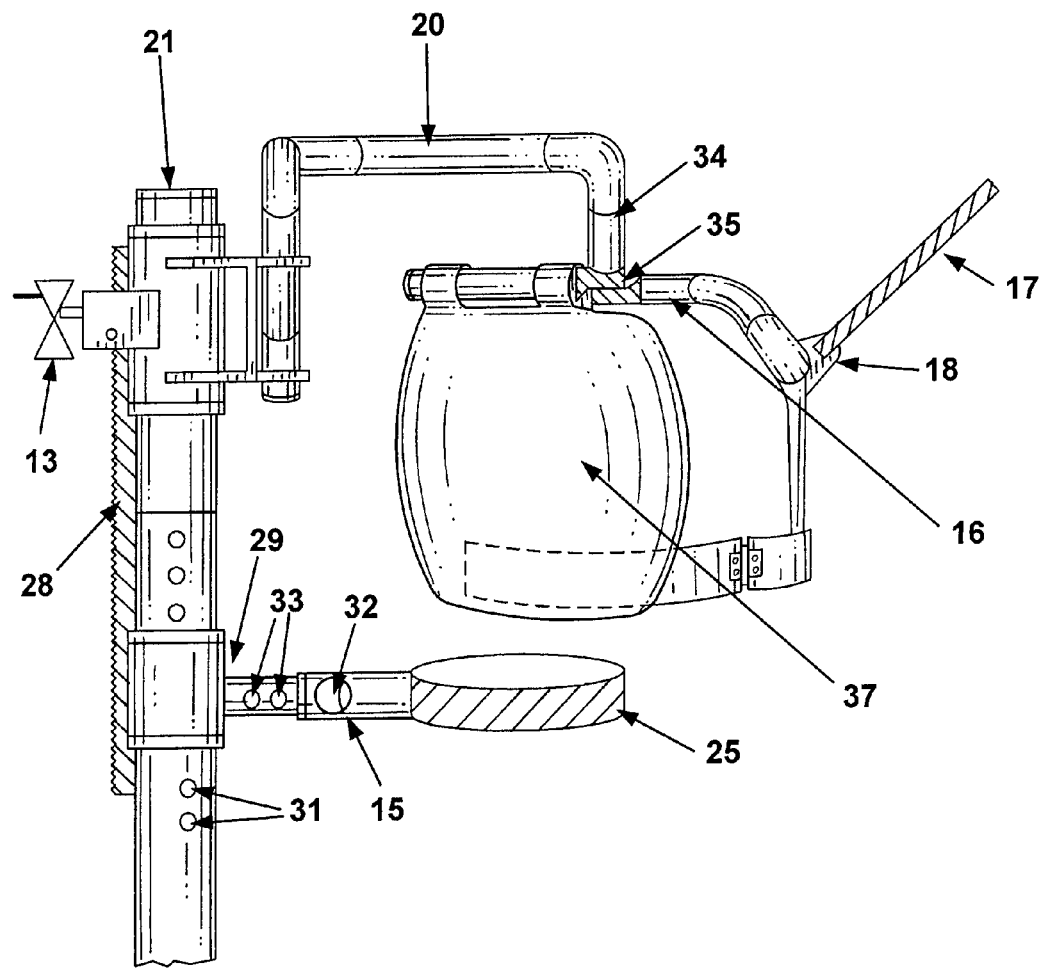
FIG. 15 is a right side view showing the shield supports and an example of an arm and shoulder protection shield supported from the upper frame, and intended to drape over the shoulders.

As shown in FIG. 15, an extra shoulder and arm shielding flap can be suspended from the outer end of the upper support 16, on both sides. FIG. 14 shows the shield on the right side of the system, but a mirror image is also supported on the left side.

Figure 16:
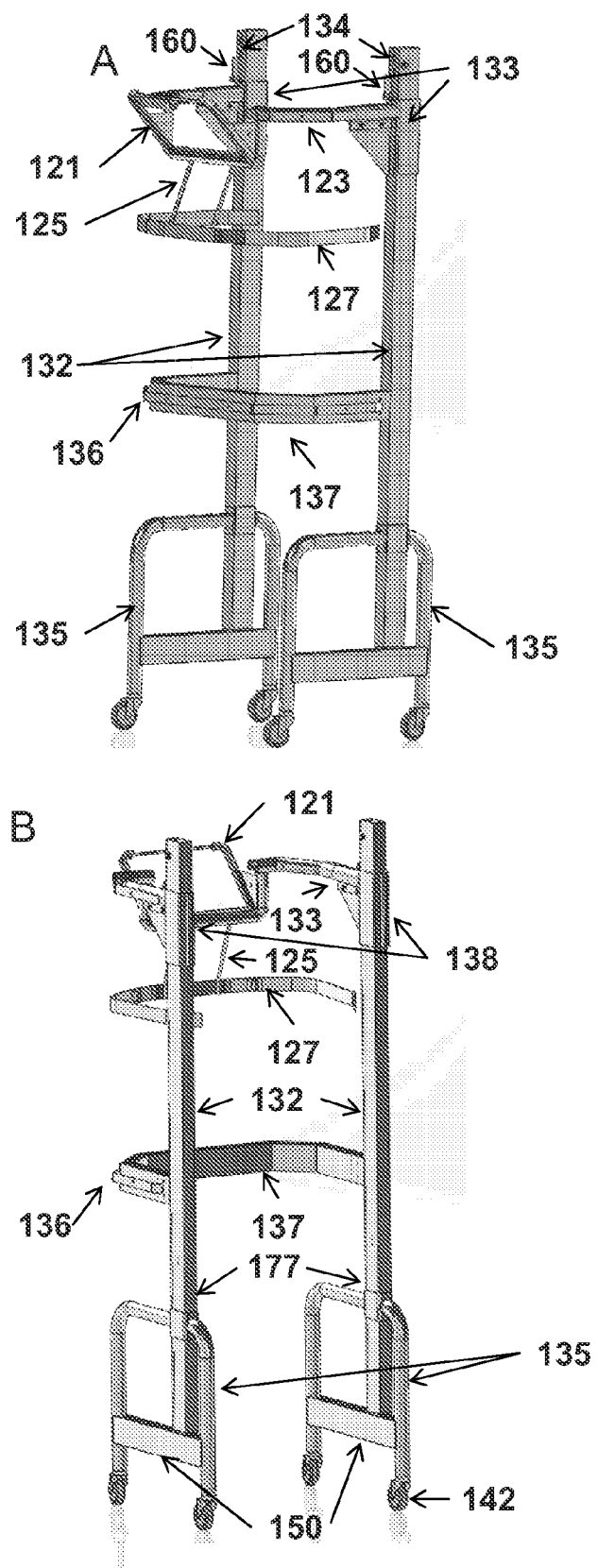

Another preferred embodiment of the robust frame is shown in FIGS. 16-18. This version of the supporting frame is designed to avoid the necessity of a swing-out assembly for user entry by providing an open rear aspect through which the assembly can be entered and exited.

This embodiment is formed of a pair of vertical columns 132, in this case each having a hollow rectangular cross-section. Each vertical column 132 is supported upon a lower frame 135, supported on two casters 142. Each frame 135 has a horizontal cross brace 150, upon which the vertical column 132 rests; the vertical column 132 also is horizontally braced by the upper portion 177 of the lower frame 135. In this embodiment, the two vertical columns 132 are rigidly connected to each other by a central frame member cross-brace 137 and an upper frame 123. The upper frame 123 are rigidly connected to and extend outwardly from a pair of sleeves 133, which are each vertically slidably connected to, and supported by one of the hollow vertical columns 132.

The sleeves 133 are each connected through a cable suspension, which in turn is connected to an adjustable counterweight assembly 147 located within each of the hollow tubing columns. This suspension allows the frame 123 to controllably move freely up and down in the vertical direction, while adjusting the counterweight allows for the balancing of the load on the frame so as to hold the frame in a desired vertical position. In the illustrated case in FIG. 17, the counterweights are individually connectable, so that depending upon the weight of the shield on the upper frame 123, the counterweight can precisely balance that weight and thus hold it at a desired height. As a safety measure, a lock can be inserted at various heights along each column to ensure there would be no undesirable vertical movement. Alternatively, clamps mounted on the rear aspect of sliding sleeves 133 can lock the upper frame 123 at any chosen height. The counterweight assemblies located within the hollow tubing columns can be connected to the slidable sleeves 133 by a cable suspension which in turn connects to pulleys 134 located at the top of the hollow tubing columns 132 along the vertical columns.

The cable and the counterweight assemblies located within the hollow tubing columns thus counterbalances the weight of the shield rendering it much easier to move the shield vertically. The counterweight assembly 41 located within the hollow supporting columns 32 permits effortless adjustment of the height of the shield to accommodate users of varying stature. The device can be used with the counterweight assembly permitting five vertical motion of the shield to accommodate variations in posture or it can be locked into position using cam levers 38 or pins located on the rear aspect of the shield supporting sleeves 33. The upper frame 123 further comprises a transparent face shield 121, facing forwardly, and suspended therefrom a throat shield 125 that, in turn, supports an upper shield holder hanger 127. An upper shield 155 hangs downwardly from the shield holder hanger 127, and is vertically adjustable so as to be able to overlap the main support brace 136, regardless of the height of the operator.

The cable and the counterweight assemblies located within the hollow tubing columns thus counterbalance the weight of the shield rendering it much easier to move the shield vertically. The counterweight assembly 41 located within the hollow supporting columns 32 permits effortless adjustment of the height of the shield to accommodate users of varying stature. The device can be used with the counterweight assembly permitting free vertical motion of the shield to accommodate variations in posture or it can be locked into position using cam levers 138 or pins located on the rear aspect of the shield supporting sleeves 133. The upper frame 123 further comprises a transparent face shield 121, facing forwardly, and suspended therefrom a throat and upper chest shield 125 that, in turn, supports an upper shield holder hanger 127. An upper shield 140 hangs downwardly from the shield holder hanger 127, and is vertically adjustable with the counterweighted upper assembly 123 so as to be able to overlap the main support brace 136, regardless of the height of the operator.

The preferred embodiment depicted in FIGS. 16-18 permits a telescoping shield configuration to provide head-to-toe shielding regardless of the height of the user. As shown in FIG. 18, a fixed lower shield 139 is attached at its upper aspect to a mounting frame 136 on the outer surface of the cross-brace 137, as is more clearly shown in FIGS. 15 and 17A. The fixed lower shield 139 extends to within 2 inches of the floor to protect the lower extremities of the user from the more intense scattered radiation directed downward from the under surface of fluoroscoped patients. To accommodate variations in the height of the user, the counterweighted vertical adjustment of the upper shield assembly 123 telescopes with respect to the lower fixed shield 139. The front upper panel 140 drapes over and overlaps the fixed lower shield 139 in the front while the side panels of the upper shield 141, overlap the fixed shield from within. This overlapping feature of the counterweighted vertical upper shield 139 ensures that the surgeon is shielded from head-to-toe, regardless of the height of the user.

It will be readily understood that the specific details of the components of the shield support described above and in the drawings are not required in order to form the present invention. It should be noted that a different shapes and different materials for the frame components may all be within the scope of this invention. It will therefore be readily understood that the present invention is not limited to the particular elements and materials shown and described hereinabove.

The various aspects, characteristics and architecture of the device of the present invention have been described in terms of the embodiments described herein. It will be readily understood that the embodiments disclosed herein do not at all limit the scope of the present invention. One of ordinary skill in the art to which this invention belongs can, after having read the disclosure, and reviewed the drawings, may readily implement the device and method of the present invention using other implementations that are different from those disclosed herein but which are well within the scope of the claimed invention, as defined by the following claims.

What is claimed is:

1. A rollable structure for suspending a heavy radiation protective garment so as to allow easy movement in a clinical environment subject to exposure to x-radiation, the structure comprising a vertically extending frame that is attachable to a user, that permits the user to move freely around the clinical environment and to perform clinical duties without having to bear the weight of the shielding garment; the frame being vertically adjustable; upper shield support surfaces for supporting the shoulder portions of a radiation protection apron, the upper support surfaces extending outwardly from the vertical frame; a rollable lower support frame for the vertical support frame, comprising a first lower frame extending forwardly from the vertically extending frame; a pair of rollers at the lower end of the first lower frame, located forwardly of the vertically extending frame and a second lower frame located at a position other than forwardly of the vertically extending frame; a second pair of rollers located at the lower end of the second lower frame; and a midbody attachment for securing a flexible belt between the vertically extending framework and the user to allow the user to walk with the framework without the use of his hands.

2. The rollable structure of claim 1, further comprising a face shield supported from the support surfaces.

3. The rollable structure of claim 1, further comprising lower support surfaces for supporting lower portions of a radiation protection apron, the lower support surfaces extending outwardly from the vertical frame below the upper support surfaces.

4. The rollable structure of claim 1 wherein the vertically extending frame is comprised of manually adjustable telescoping tubes.

5. The rollable structure of claim 1, wherein mutually telescoping hollow tubes incorporate an expandable internal hollow spaces responding to a change in internal pressure inside of the hollow mutually telescoping tubes.

6. The rollable structure of claim 4, further comprising a pneumatic pressure pump operably connected to the internal hollow spaces to increase and reduce pressure within the hollow tubes, so as to cause the tubes to vertically move upward and downward, respectively, in response to an increase or reduction in the internal pressure of the inner hollow spaces.

7. The rollable structure of claim 6, further comprising electrically powered motor means for operating the pneumatic pressure pump or internal cables that operate the telescoping motion.

8. The rollable structure of claim 1, constructed of a heavier base frame containing a single support column extending upward to support the upper frame elements.

9. The rollable structure of claim 8 further comprising a second shield support extending from and supported by the upper shield support, and further comprising a ratcheting rack and pinion gear mechanism for adjusting the vertical height of the two shield supports.

10. The rollable structure of claim 9 where the upper frame suspending the protective garment swings outward to permit the user in sterile garb to enter the frame from behind the apron.

11. The rollable structure of claim 8 where the apron is enclosed with a sterile drape that envelops the external surfaces of the protective garment.

12. The rollable structure of claim 8 where the radiation protective transparent face shield is attached to the front of the upper garment support arm with brackets permitting adjustment of the angle of the face shield with respect to the vertical axis.

13. The rollable structure of claim 8, further comprising a horizontal adjustment mechanism for adjusting the distance of the waist attachment bracket from the apron shield.

14. The rollable structure of claim 1, constructed of a heavier base frame containing two hollow support columns extending upward to support the upper frame elements permitting the user to enter the shield from the rear aspect without obstruction.

15. The rollable structure of claim 14 further comprising a second shield support extending from and supported by the upper shield support, and further comprising a pulley suspended counterweight mechanism enclosed within the support column for easily adjusting the vertical height of the two shield supports.

16. The rollable structure of claim 15 where the force needed to balance the weight of the assembly is partially comprised of a lighter counterweight force together with one or more constant force flat coiling springs exerting a downward force on the counterweight assembly from the bottom aspect of the support column.

17. The rollable structure of claim 14 where the apron is enclosed with a sterile drape that envelops the external surfaces of the protective garment.

18. The rollable structure of claim 14 where the waist attachment bracket is eliminated and the mobile assembly is moved by the user with a pair of forearm-rests enclosed within the upper shield assembly.

19. The rollable structure of claim 1 where a vertically adjustable, removable seat is attached to the vertical support columns so that the user can perform procedures from a seated position within the shield enclosure.

20. The rollable structure of claim 14 where a vertically adjustable, removable seat is attached to the vertical support columns so that the user can perform procedures from a seated position within the shield enclosure.

* * * * *